| United States Patent [19] | [11] | 4,212,368 |
|---|---|---|
| Allen | [45] | Jul. 15, 1980 |

[54] ANGULARLY RELATED DUAL STETHOSCOPE HEAD

[76] Inventor: Derek R. Allen, 27 Point Loma, Corona del Mar, Calif. 92625

[21] Appl. No.: 885,883

[22] Filed: Mar. 13, 1978

[51] Int. Cl.$^2$ .......................... A61B 7/02; H04R 25/00
[52] U.S. Cl. ...................................... 181/131; 181/137
[58] Field of Search ................................ 181/131, 137

[56] References Cited

U.S. PATENT DOCUMENTS

| 3,124,211 | 3/1964 | Cefaly | 181/131 |
| 3,630,308 | 12/1971 | Ravin | 181/131 |
| 3,767,003 | 10/1973 | Shacklock | 181/137 |

Primary Examiner—John Gonzales
Assistant Examiner—Benjamin R. Fuller
Attorney, Agent, or Firm—George F. Bethel; Patience K. Bethel

[57] ABSTRACT

A stethoscope head having a bell and a diaphragm. The bell is offset from the diaphragm axis. The bell axis intersects the diaphragm axis at an acute angle of not less than twenty degrees or more than seventy degrees, and preferably at thirty degrees. A selectively movable valve is provided to connect the bell and the diaphragm, individually, to an airway which may be connected to a sound tube leading to binaurals. The valve comprises a cylindrical spool seated and totally supported within a cylindrical bore in the head body.

6 Claims, 4 Drawing Figures

ANGULARLY RELATED DUAL STETHOSCOPE HEAD

BACKGROUND OF THE INVENTION

Field of the Invention

Most stethoscopes used today have a dual chest-piece type of head with a switch valve for selectively connecting the sound tube either to a low frequency bell or to a high frequency diaphragm. Both the bell and the diaphragm are necessary when a person skilled in heart problems desires to listen very closely to the heart. For example, the diaphragm is useful in listening to sounds emanating from a heart in the range of 100 to 2,000 Hz. The diaphragm may be rather large, since it is not necessary that is be sealed to the skin of the patient; it is only necessary that it touch the patient's skin on at least one portion of the diaphragm surface.

On the other hand, the bell must be sealed about its periphery to a patient's skin since the skin itself is used as a diaphragm. Consequently, the bell is useful in the low frequency range of 50 to 150 Hz. It has been found that the deeper the bell is, the better response it actually provides to the listener within this frequency range.

In prior art stethoscopes, in order to have a deep bell, it was necessary that the bell axis be offset from the diaphragm axis 90°. A valve was situated on the intersection of the axis of the bell and the diaphragm. Thus, either the bell or the diaphragm could be shut off when not in use to eliminate spurious sounds. While this arrangement produced an excellent stethoscope with high acoustical quality, it resulted in a large mass in the head, making the total stethoscope very heavy and, consequently, difficult both to wear and to carry. Further, such stethoscopes required that the doctor or listener use two hands when switching from one microphone mode to the other. In other words, if the listener were employing the diaphragm and wished to employ the bell, he would have to use his free hand to operate the switch. If the patient required support, the presence of a nurse or other attendant was therefore required. Further, this stethoscope suffered from the deficiency of being rather difficult to employ in both modes in a confined space, such as under a shirt, or within a brassiere. Consequently, it was almost always necessary for the patient to at least partially disrobe in order for the doctor to listen to the patient's heart in both of the head modes.

In the more recent past, it has become somewhat common to provide a dual head in which the bell and the diaphragm are coaxially aligned on the opposite sides of the head body. An example of such a stethoscope has been shown in my prior U.S. Pat. No. 3,472,335. In that patent, a movable switch was positioned near the axis of the head to allow the listener to use one hand when switching from one microphone mode to the other. However, in order to be totally practical, that head resulted in a compromise which has proven to be somewhat unacceptable. To prevent the thickness of the head from becoming so cumbersome as to be impractical, it was necessary to reduce the depth of the bell. As a result, the stethoscope is unable to detect and transmit sounds generated by the heart in the lowest desirable frequencies.

Consequently, it has become necessary to provide a dual head having a bell with the maximum possible depth. It has been preferred that such a head have a relatively low mass to provide comfort for the wearer and ease for the person carrying the stethoscope. It is also preferred that such a stethoscope have a minimum overall height in order to make the stethoscope easier to use with a patient who has remained clothed, etc.

SUMMARY OF THE INVENTION

The present invention provides a stethoscope head which eliminates the prior art deficienies described above and fulfills each of the requirements set forth in the preceeding paragraph.

Further, the present invention results in such a stethoscope head which allows the use of a plastic injection molded bell, thereby reducing the chill which a patient may experience when the stethoscope is applied to his skin.

In the preferred embodiment of the present invention, a stethoscope head may be constructed so that the bell axis is neither perpendicular to nor coaxial with the diaphragm axis. Rather, the two axes may intersect at an acute angle. It has empirically been determined that the preferred angle between the two axes is 30°, although it may be anywhere from 20° to 70°. Offsetting the bell from the diaphragm axis allows the bell to be placed near the front of the head, significantly facilitating the ability of the listener to seal the head comfortably against the patient's skin, or even reverse the head within a confining piece of clothing to utilize the diaphragm.

Further, the present invention may employ a cylindrical valve spool which may be supported substantially about its entire periphery within the valve body. Consequently, the valve spool may be very closely sealed to its valve seat, eliminating acoustical leaks and sound transmission defects within the instrument.

An airway, or sound tube, may be fixedly connected to the valve spool, allowing the passage of acoustical waves through the valve spool and into the tube leading to the binaurals. The airway or sound tube also acts as a lever to facilitate rotation of the valve spool between predetermined limits in which the latter is in acoustic communication with the bell or the diaphragm. In other words, the listener can utilize one hand to body hold the head and to change it from one mode to the other. Consequently, while the doctor may be providing support for a patient with his left hand, for example, he may use his right hand to both hold the head and to change the acoustical communication when he reverses it from one mode to the other.

If desired, structure may also be provided to releasably lock the valve spool in the positions in which the acoustical passageways are joined, thus relieving the listener from the necessity of holding or checking the valve connection.

Upon review of the following detailed description, taken together with the accompanying drawings, those skilled in the art will appreciate a number of other significant advantages inherent in a head formed in accordance with the present invention. Similarly, they will realize that the present invention may be employed in a wide variety of structures, many of which may not even resemble that depicted here, but which nevertheless, will employ the spirit and teaching of the invention.

DESCRIPTION OF THE PREFERRED EMBODIMENTS

Figure 1:
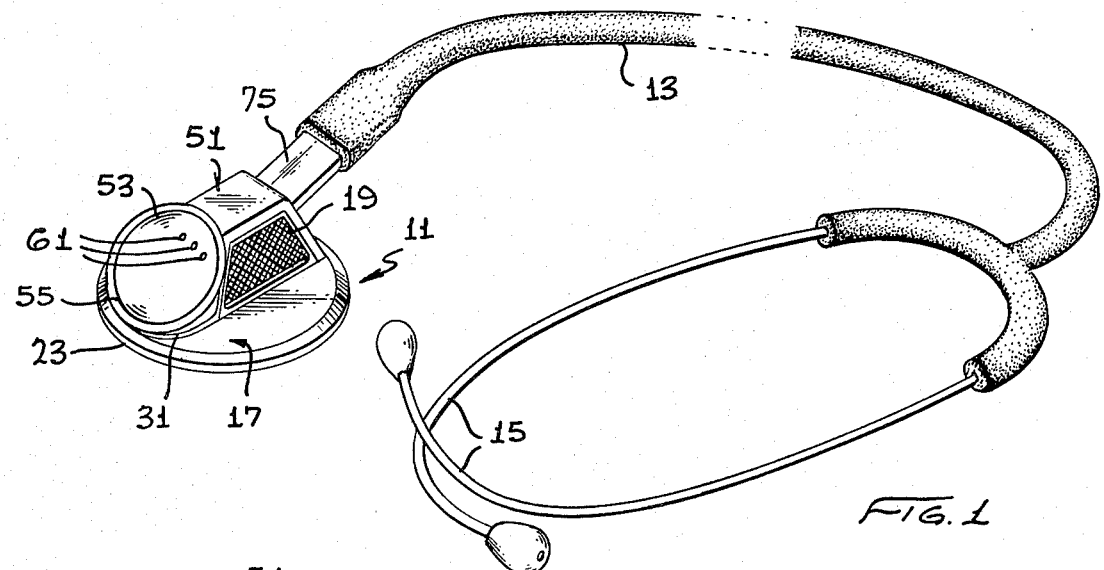
FIG. 1 comprises a perspective illustration of a stethoscope employing the present invention.

As shown in FIG. 1, a stethoscope head 11 may be suitably attached to a flexible sound tube 13 which leads and is connected to binaurals 15 which may be placed in the ears of a listener in a well known manner.

Figure 2:
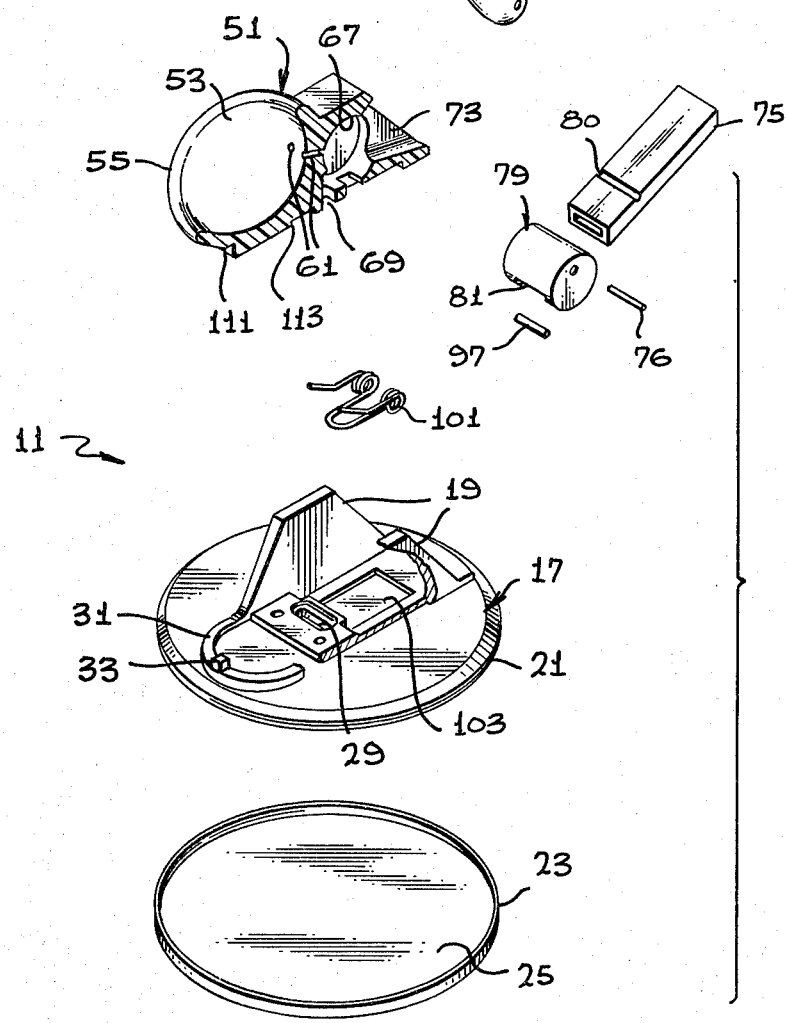
FIG. 2 comprises an exploded view, with certain elements in section, in order to depict the structural relationships of the preferred embodiment.

Referring now to the four figures together, it may be seen that the head 11 may include a first body member 17 having a pair of upstanding ears or flanges 19, only one of which is shown completely in FIG. 2. The body member 17 may be provided with a periphery 21 upon which a ring 23 may be threadedly or otherwise suitably mounted in order to seal a diaphragm 25 between the ring and the body member. Consequently, a sound chamber 27 may be formed between the diaphragm and the body member and in communication with a first passage 29 in the body member.

On the upper face of the body member 17 there may be provided various locating structures, including A lip 31 with a key-like structure 33 for suitably locating and supporting an upper body member 51. It should be noted that while the first body member 17 may be of plastic, stainless steel, or some other desired material, the second body member 51 may be a plastic injection molded material, if desired.

Since the body member 51 may be injection molded, it will be realized that the bell 53 will not create much chill in the body of the patient when the head is placed into position, assuming that the head has not been subject to other than normal carrying about the neck or in the pocket of the user.

The second body member may include an integral bell 53 having a lip or periphery 55. The bell may include a central chamber 57 (FIGS. 3 and 4) which may be considered to be developed about an axis 59. A slot or series of openings 61 may be provided in the inner wall 57 of the bell for communication of the bell interior with an acoustical passage 65 within the body member 51.

The body member 51 may also be provided with a lateral cylindrical bore 67 in communication with the passage 65. Bore 67 may also communicate with a passage 69 which in turn, may be in sealed communication with the passage 29 when the body members 17 and 51 are assembled as illustrated in FIGS. 3 and 4.

Extending from the cylindrical bore 67 toward the rear of the body member 51, an opening 73 may be provided through which a sound tube or airway-means 75 may extend for connection with the tube 13. The airway may be fixedly connected, at its inner end by a key or pin 76 passing through opposite semi-circular grooves 78 and 80, to a cylindrical valve spool 79 positioned within the bore 67 in close, sealing realtionship therewith. A radial passage 81 may be provided in one side of the spool 79 for alignment with the airway central passage. The passage 81 may terminate in a squared bore 83 in the spool into which the inner end of the airway member 75 may be sealingly seated.

Figure 3:
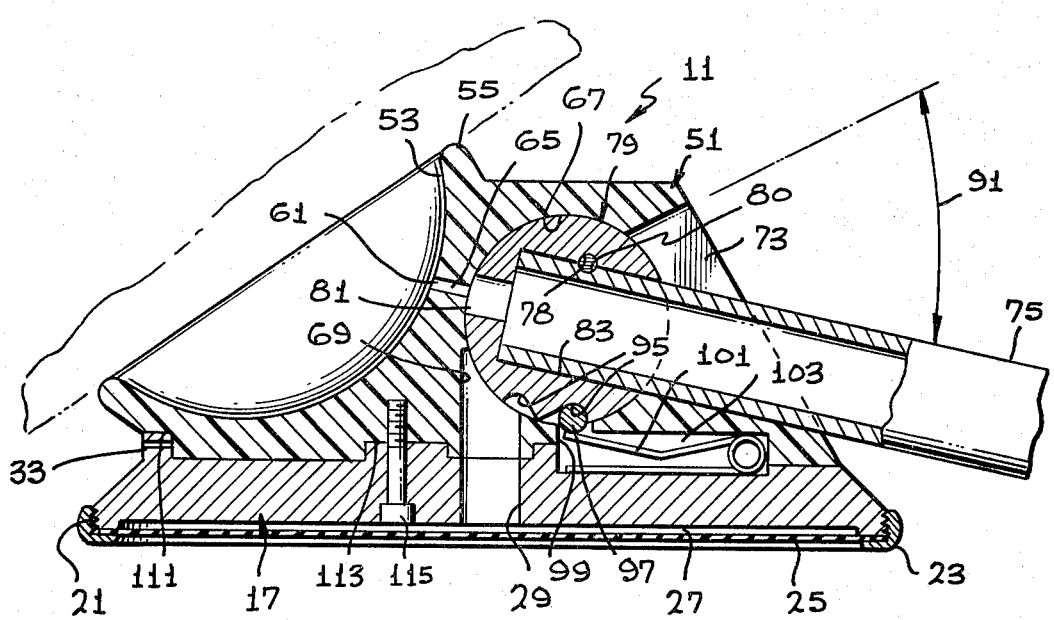
FIG. 3 comprises a vertical sectional view of the head formed in accordance with the present invention being utilized in the bell mode; and, FIG. 4 comprises a view, similar to FIG. 3, with the head being employed in the diaphragm mode.
Figure 4:
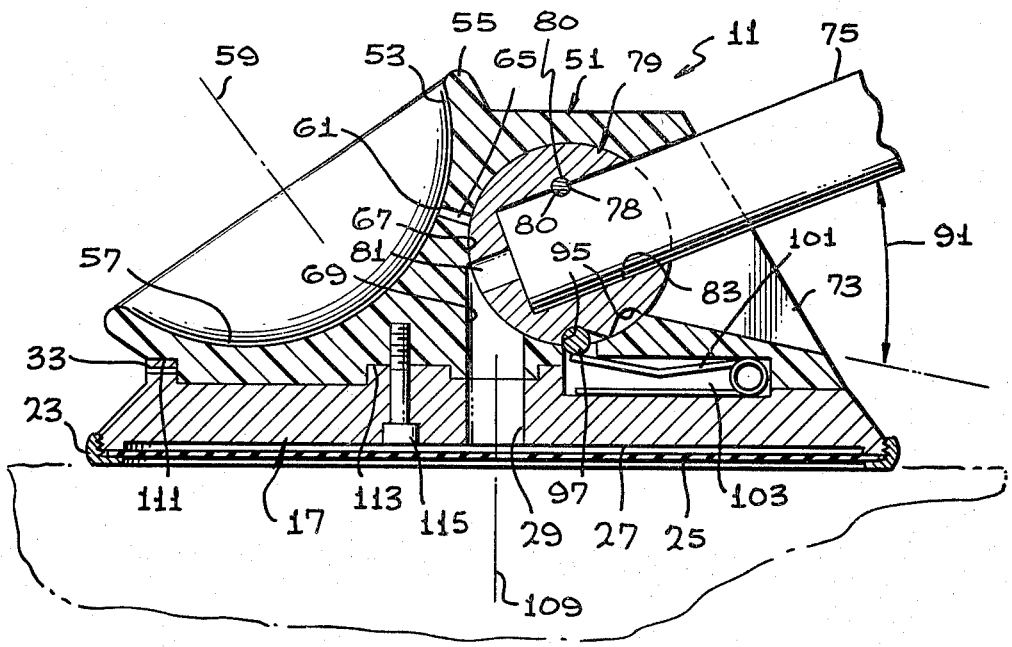

As illustrated in FIGS. 3 and 4, the airway member 75 may be rotated up or down along the arrow 91 to alter the acoustical connection between the passageway 81 and the bell of the diaphragm. Consequently, the tubular element 75 serves not only to form an airway through which acoustical waves can be transmitted to the binaurals, but also acts as a lever to cause rotation of the valve spool 79. The listener may thus use only one hand to hold the head in place against the patient, as well as to alter the position of the valve spool in the manner illustrated.

In order to obviate the possibility of inadvertent movement of the valve spool 79, means may be provided to releaseably fix the spool in the two illustrated positions. In this preferred embodiment, such means may comprise a pair of lateral detent grooves 95 formed in the periphery of the valve spool 79. A pin or bar 97 may be positioned within an opening 99 in the body member 51 and urged into the grooves 95 as they are aligned therewith, by means of a spring 101 located within a compartment 103 formed between the body members 17 and 51. Consequently, as the airway 75 is utilized as a lever, the pin 97 will act against the force of spring 101 as it is cammed downwardly by the ridge formed between the adjacent grooves 95. Continued movement of the airway 75 will then result in the pin 97 being moved into the newly aligned groove 95. The spring and pin will thus serve to positively lock the spool 79 against inadvertent rotation until sufficient force is exerted against the airway lever 75.

The undersurface of the body portion 51 may be provided with suitable configuration to conform to the guide 31 and key 33. For example, as illustrated in FIGS. 3 and 4, the body member 51 may be provided with a keyway 111, a recess 113, etc. The parts may therefore be properly mated and fastened together by any suitable means, such as bolts 115 which pass through the body member 17 and are threadedly connected to the body member 51. In other words, the bolts 115 may be put into position and the diaphragm 25 and ring 23 then installed.

As shown particularly in FIG. 4, the bell axis 59 and the central axis 109 of the diaphragm and the head per se, intersect at an acute angle. Preferably, the angle between the axes is approximately 30° but it may be as much as 70°, or as little as 20°. In any case, in this illustrated embodiment, the intersection of the axes 59 and 109 is on the side of the diaphragm opposite the chamber 27. It can be seen, however, that as the axis 59 moves closer to being coaxial with the axis 109, either the depth of the bell 53 must be reduced, or else the thickness of the head 11 must be increased. Similarly, if the axis 59 were rotated counterclockwise about the point of interception of the axes, either the radius of the bell lip 55 would have to be reduced significantly, or else the thickness of the head would also have to be increased.

In other words, proper selection of the acute angle between the two axes allows the bell to be produced with the maximum pratical depth, while the microphone itself is at the minimum practical thickness. It should also be noted that the acoustical passageway 61 leading from the bell to the switching valve need not be at the bottom or axis of the bell; it has been found that such an offsetting results in no acoustical deterioration.

It can also be seen by a comparison of FIGS. 3 and 4 that the particular relationship of the valve spool and the various acoustical passages clearly facilitates handling of the microphone by the listener. For example, when the bell is placed against the listener's body as illustrated in FIG. 3, the airway-lever 75 is in the downward position, thus facilitating the listener's handling and holding of the head. Similarly, when the diaphragm is held against the patient's body as illustrated in FIG. 5, the airway-lever 75 is in the upper position, also facilitating the holding of the head against the patient. Since the thickness and the resulting mass of the microphone are reduced through the employment of the present invention, it will be quite easy for the listener to hold the head in a confined space underneath the shirt or within the brassiere of a patient without creating any discomfort. Further, the listener can reverse the head quite easily, without disturbing the patient, and usually without having to remove it from within the patient's clothing, thus simplifying his task and allowing the examination to be accomplished more quickly.

Having now reviewed the detailed description of this preferred embodiment of the invention, those skilled in the art will realize that a wide variety of structures may be employed utilizing these teachings. Many of those additional embodiments may not even resemble that depicted and described here, but such differences will not remove them from the scope of the invention as defined in the following claims.

I claim:

1. A stethoscope head comprising:
   a low frequency sound receiving bell having,
   a bell axis and a concave cross-sectional configuration forming a bowl-like member;
   a high frequency sound receiving diaphragm having,
   a diaphragm axis;
   a body joining and supporting said bell and said diaphragm such that said bell axis intersects said diaphragm axis at an acute angle, said body including,
   a valve seat;
   a first airway joining said diaphragm with said valve seat;
   a second airway joining said bell with said valve seat and being offset from said bell axis, said airway being formed of a series of openings of substantially smaller diameter than the diameter of said first airway;
   a valve spool operatively mounted in said valve seat having a central axis outside of said bell axis and said diaphragm axis;
   a flattened sound tube passing through said valve spool and extending from said body member to act as a lever whereby said spool can be rotated within said valve seat to selectively communicate said sound tube with said first and second airways, said sound tube having an operative axis outside of the respective bell axis and said diaphragm axis.

2. The head of claim 1 wherein,
   said valve means further comprises:
   detent means within said spool for selectively locking said spool in a position to operatively communicate said sound tube in said spool with said bell and said diaphragm airways.

3. The head of claim 2 wherein,
   said body comprises:
   a first portion including said bell and said valve means; and
   a second portion including said diaphragm and fastenable to said first portion.

4. The head of claim 3 including:
   locking bar means; and
   means for urging said locking bar means into cooperative relationship with said detent means.

5. A stethoscope head comprising:
   a first body member having,
   a central axis;
   a diaphragm in substantially perpendicular relationship to said central axis;
   a sound chamber adjacent said diaphragm; and,
   a second body member having a sound receiving bell formed in a concave cross-sectional dish-shaped configuration having a bell axis;
   a lateral cylindrical bore in said second body member;
   a cylindrical valve spool in said cylindrical bore having a radial passage therethrough and having an axial center which is outside of said bell axis and said diaphragm axis;
   a flattened sound tube within said radial passage, having an operative axis outside the respective bell axis and diaphragm axis;
   means to secure said sound tube within said valve spool radial passage;
   an opening in said second body member through which said sound tube can extend, and act as a lever for rotation of said valve spool;
   first passage means for communicating said diaphragm with said sound tube upon suitable rotation of said valve spool;
   second passage means offset from said bell axis for communicating said bell with said sound tube upon suitable rotation of said valve spool, and comprising a series of openings of substantially smaller diameter than the diameter of said first passage means;
   spring loaded detent means for selectively locking said spool in a position to separately communicate said sound tube with said first and second passage means;
   means to secure said first body member to said second body member.

6. The head of claim 5 including,
   said detent means for releasably locking said valve spool means in at least two positions for selective connection between the sound tube therein and said first and second passages comprise:
   a pair of lateral detent grooves in the periphery of said valve spool;
   a ridge formed between said grooves;
   a compartment in proximate relation to said grooves;
   a spring in said compartment; and,
   a pin positioned for biasing by said spring within one of said lateral detent grooves, said pin being moved from one of said grooves to another by urging with said ridge upon rotation of said valve spool.

* * * * *